United States Patent [19]

Giglio et al.

[11] Patent Number: 5,231,974

[45] Date of Patent: Aug. 3, 1993

[54] SELF RETAINING RETRACTOR

[76] Inventors: Steven R. Giglio, 1920 Stuart Ave.; Glen J. Schwartzberg, 6944 Chandler Dr., both of Baton Rouge, La. 70808

[21] Appl. No.: 890,962

[22] Filed: May 29, 1992

Related U.S. Application Data

[63] Continuation-in-part of Ser. No. 708,300, May 31, 1991, abandoned.

[51] Int. Cl.⁵ .............................................. A61B 17/02
[52] U.S. Cl. ................................................... 128/20
[58] Field of Search ......................................... 128/20

[56] References Cited

U.S. PATENT DOCUMENTS

| 1,919,120 | 7/1933 | O'Connor | 128/20 |
|---|---|---|---|
| 2,053,868 | 9/1936 | Grosso | 128/20 |
| 2,250,605 | 7/1941 | Rubin | 128/346 |
| 2,623,517 | 12/1952 | Barlow et al. | 128/20 |
| 2,701,562 | 2/1955 | Michael | 128/20 |
| 2,812,758 | 11/1957 | Blumenschein | 128/20 |
| 2,893,378 | 7/1959 | Cooper | 128/20 |
| 3,040,739 | 6/1962 | Grieshaber | 128/20 |
| 3,129,706 | 4/1964 | Reynolds, Jr. | 128/20 |
| 3,384,078 | 5/1968 | Gauthier | 128/20 |
| 3,394,700 | 7/1968 | Yamamoto | 128/20 |
| 3,515,129 | 6/1970 | Truhan | 128/20 |
| 3,782,370 | 1/1974 | McDonald | 128/20 |
| 3,998,217 | 12/1976 | Trumbull | 128/20 |
| 4,151,837 | 5/1979 | Millard, Jr. | 128/12 |
| 4,421,107 | 12/1983 | Estes | 128/20 |
| 4,434,791 | 3/1984 | Darnell | 128/20 |
| 4,852,552 | 8/1989 | Chaux | 128/20 |
| 4,924,857 | 5/1990 | Mamoodian | 128/20 |
| 4,926,849 | 5/1990 | Downey | 128/20 |
| 4,932,395 | 6/1990 | Mehdizadeh | 128/20 |
| 4,949,707 | 8/1990 | LeVahn et al. | 128/20 |
| 4,971,037 | 11/1990 | Pelta | 128/20 |
| 4,971,038 | 11/1990 | Farley | 128/20 |
| 4,989,587 | 2/1991 | Farley | 128/20 |
| 5,052,373 | 10/1991 | Michelson | 128/20 |

FOREIGN PATENT DOCUMENTS 2730164 8/1978 Fed. Rep. of Germany ........ 128/20

OTHER PUBLICATIONS

Fackler, M. L., "Extending the Usefulness of Self-Retaining Retraction," *The American Journal of Surgery*, vol. 129, pp. 712-715, Jun., 1975.

Minnesota Scientific, Inc. OMNI-TRACT 3004 Abdominal-Vascular System, Copyright Nov., 1986.

Codman & Schurtleff, Inc. Brochure, John Bookwalter, M. D., "Good Exposure Is The Key To Good Surgery".

*Primary Examiner*—John J. Wilson
*Attorney, Agent, or Firm*—Pravel, Hewitt, Kimball & Krieger

[57] ABSTRACT

A self-retaining retractor which can be assembled and used without assistance, retracting a surgical incision, retaining the incision open, and providing for retraction of internal organs and tissues inside the patient's body through the open incision. Flexible, resilient incision retractor paddles are placed into the incision, a rigid frame consisting of two interlocking halves is laid longitudinally over the incision. The incision retractor paddles in the incision are manually clipped to each frame half then the frame halves are opened to the desired extent. Incision retractor paddles and frame provide the apparatus stability for retraction of internal organs and tissues through the open incision by the addition of mounting jigs containing attachment posts onto mounting means which radiate outward from the frame. Internal organ and tissue retraction means are affixed to the attachment posts.

11 Claims, 6 Drawing Sheets

SELF RETAINING RETRACTOR

CROSS REFERENCE TO RELATED APPLICATIONS

This is a continuation-in-part of copending U.S. patent application Ser. No. 07/708,300, filed May 31, 1991, now abandoned which is incorporated herein by reference.

BACKGROUND OF THE INVENTION

1. Field of the Invention

The present invention relates to surgical retractor apparatus and in particular to self-retaining surgical retractor apparatus which retract a surgical incision, retain the incision open and retract organs and tissues inside the body through the open incision.

2. General Background

Surgical "retraction" is the drawing back of body tissue. When the operation involves making an incision, the incision itself often must be retracted, and during surgery, internal organs and tissues are intermittently retracted through the opening created by the retracted incision.

An assistant's fingers are capable retractor paddles; however, greater technical ease should be available through the use of mechanical retractor systems. Mechanical retractor systems can be divided into two major groups: externally mounted "fixed" to the operating table, and self-retaining retractors.

Since the tactile sensitivity present in the assistant's fingers during hand retraction is lacking in mechanical retractor systems, the use of mechanical retraction increases the risk of tissue trauma; however, the mechanical system can be more stable and possesses infinite endurance.

The mechanical retractor systems attached to the operating table present the same type of physical obstruction to the surgeon's movement as presented by the assistant's body, arms and hands since the externally fixed retractor systems mimic the assistant's body, arms and hands through the use of a vertical column, supporting arm(s) or ring and retractor paddles attached thereto. Examples of this art include the systems illustrated in U.S. Pat. Nos. 4,949,707; 4,971,038 and 4,971,037. The retractor paddles, support arms or ring and vertical column in these apparatus are adjustable in multiple planes and axes of motion; however, these retractor paddles are not all independently adjustable in the vertical plane. Movement of a support arm or ring of these apparatus necessitates movement of all retractor paddles attached thereto.

Despite the advantage of adjustability in all planes and axes of motion, the externally mounted retractors all share these disadvantages:

A. Size and location of numerous pieces create an impediment to movement of surgeon and his assistant(s);
B. Length of time required for assembly;
C. Require assistance in assembly, and can break sterile field;
D. Retractor paddles are not independently adjustable in the vertical plane;
E. Planned patient movement requires time consuming disassembly and reassembly;
F. Involuntary patient movement can injure retracted tissue and organs;
G. Packing material (sponges) often required to cushion retractor paddles can cause injury;
H. Size and number of pieces increases cost;
I. Technical surgical ease restricted by height, location, size and multiplicity of pieces;
J. Disassembly in an emergency is time consuming;
K. Size of pieces makes sterilization difficult; and
L. Paddles are not interchangeable between different manufacturers.

Ideally, mechanical retractors both externally mounted and self-retaining need to provide for internal organ and tissue retraction, be quickly and easily assembled, positioned and repositioned in all planes and axes of motion, present as little obstruction to the surgeon's movement as possible, protect the sterile field, diminish the risk of tissue trauma, and yet be stable enough to function adequately while reducing the need for assistance.

Self-retaining retractors present less obstruction to the surgeon's movement and do not risk breaking the sterile field; falls far short of satisfying the surgeon's need for internal organ and tissue retractor paddles that can be quickly, independently, easily and safely adjusted without assistance in all planes and axes of motion.

The following patents illustrate self-retaining retractors that are capable of retraction of the surgical incision only or retraction of a body orifice only: U.S. Pat. Nos. 4,924,857; 2,893,378; 2,701,562; and 1,919,120.

The following patents illustrate self-retaining retractors that provide for retraction of an incision plus the retraction of organs and tissue through the opening created by the incision; however, the retraction paddles in these apparatus are not adjustable in more than one plane and perhaps one axis of motion: U.S. Pat. Nos. 4,421,107; 3,394,700; 3,129,706; 2,812,758; 2,623,517; and, 2,053,868.

Certain of the advantages and disadvantages of self-retraining retractors available on the market such as the "Weitlaner" (scissor action); "Brunschwig"; "Wilkinson" and "Wexler" (ring type); and "Balfour" (slide action) are discussed in the medical literature. Fackler, M. L., "Extending the Usefulness of Self-Retaining Retraction," The American Journal of Surgery, Vol. 129, pp. 712-715, June 1975.

Self-retaining retractors that have attempted to provide for internal organ and tissue retraction through the open incision have failed to permit quick, independent, easy and safe adjustment of internal organ and tissue retractor paddles in all planes and axes of motion, and in effect the prior art is either ineffectual or unsafe, or both since these paddles are not easily adjustable in the vertical plane and such internal organ and tissue retractor paddles must traverse over (or through) internal tissue before reaching the desired location along the retractor handle and/or frame. The retractor paddle depth is not highly variable and the retractor paddles' location on the retractor frame is limited.

This invention merges the advantages inherent in the externally mounted retractor systems with the advantages inherent in the self-retaining retractors while eliminating the disadvantages of each.

This invention achieves the above stated advantages while eliminating numerous disadvantages by recognizing that prior self-retaining retractors could not safely and effectively retract an incision and retract organs and tissue through the open incision utilizing paddles which are not discrete and which can only be attached on or inside the retractor frame. Another reason prior self-retaining retractors cannot safely and effectively retract both the incision and internal organs lies in the fact that the incision retractor paddles also stabilize the apparatus, and effective stabilization requires the prior apparatus to use multiple incision retractor paddles occupying a large part of the retractor frame capacity. This limitation is absent in the externally mounted retractors where retractor arms or ring are stabilized some distance away from the incision so that fewer incision retractor paddles are required, and incision retractor paddles are discrete, therefore, the arms or ring have ample space to accommodate incision retractor paddles and internal organ retractor paddles.

Due to the above described inherent design deficiencies, the prior self-retaining retractors share many of the following disadvantages:

A. Internal organ and tissue retractor paddles can neither be moved independently nor in all planes and axes of motion creating risk of tissue injury and limiting technical surgical ease;
B. Incision retractor paddles concentrate stress or overlap or are difficult to set up and move risking tissue injury;
C. Incision retractor paddles and internal organ and tissue retractor paddles are not discrete; therefore, neither the incision retraction function nor internal organ and tissue retraction function are carried out with a high degree of surgical ease.
D. Uneven opening of the incision;
E. Assistance required;
F. Non-conformity to many surgical procedures;
G. Non-conformity to many patient sizes; and
H. Do not accommodate retractor paddles supplied by other manufacturers.

SUMMARY OF THE PRESENT INVENTION

Therefore it is an object of this invention to provide a self-retaining retractor which can retract a surgical incision without assistance, retain the incision open, stabilize the apparatus, and retract without assistance internal organs and tissue through the opening created by the incision.

Another object of this invention is to provide a self-retaining retractor that is less obstructive to the surgeon's movement than externally mounted retractors.

Another object of this invention is to provide a self-retaining surgical retractor which is capable of internal organ and tissue retraction through the opening created by the incision which is safe and effective. This is to be accomplished by locating attachment means for internal organ and tissue retractor paddles on posts which themselves are on mounting jigs which ratchet in and out on mounting means which radiate from the outside of the retractor frame, thereby allowing safe, easy and independent movement of internal organ and tissue retractor paddles in all planes and axes of motion, yielding the highest possible technical surgical ease.

It is also an object of this invention to provide internal organ and tissue retraction using retractor paddles from various manufacturers that are independently adjustable in all planes and axes of motion.

It is a further object of this invention to provide incision retractor paddles of different depth and (combined) lengths to accommodate various patient sizes and incision lengths, respectively, and varied surgical procedures.

Another object of this invention is to provide incision retractor paddles that retract the incision, retain the incision open and stabilize the apparatus, which incision retractor paddles are discrete from internal organ and tissue retractor paddles.

It is a further object of this invention to provide incision retractor paddles that attach to the retractor frame with easy to connect and disconnect flexible, resilient clips.

It is also an object of this invention to provide incision retractor paddles with outwardly curved bottom edge sections which are in contact with the internal surface of the integument thereby providing the apparatus with additional stability against lifting and torsional forces which can occur during internal organ and tissue retraction.

It is a further object of this invention to provide incision retractor paddles which do not unduly concentrate stress, but evenly distribute stress along the length of the incision and depth of the integument.

It is also an object of this invention to provide attachment means which accommodate the handles of internal organ and tissue retractors provided by other manufactures.

It is also an object of this invention to provide a means of retracting and retaining open an incision without assistance and thus stabilizing the retractor apparatus by first inserting incision retractor paddles into an incision, placing the retractor frame over and outside the incision paddles and then manually clipping the incision paddles onto the retractor frame, and then pulling the frame halves open, and thus retracting and retaining the incision.

A further object of this invention is to provide a self-retaining retractor which can use internal organ and tissue and other types of retractor paddles provided by other manufacturers.

Other objects, advantages and novel features of the present invention will become apparent to those skilled in the relevant art and to others from the following detailed description of the invention when considered in conjunction with the accompanying drawings.

Accordingly, a self-retaining retractor is disclosed comprising a retractor frame consisting of interlockable frame halves, the frame halves are provided at each end with posts and borings of matching dimension and cross section, the posts and borings are aligned so as to mate together, said posts are provided with ratchet grooves and ratchet stops, the ratchet grooves are acted upon by a tensioned ratchet clip which allow outward movement and retard inward movement; the frame halves are assembled by inserting the posts into the bores and by drawing back the ratchet clips and mating the halves by pushing them together. Two or more flexible, resilient incision retractor paddles are placed inside the patient's incision with the bottoms of paddles' attachment means lying outside the body. The incision retractor paddles' attachment means face away from each other toward the inside face of the retractor frame, which is laid longitudinally over the incision outside the incision retractor paddles. Incision retractor paddles vary in length (or number) and depth to accommodate varying length incisions and depth of integument being retained open. The surgeon manually clips the incision retractor paddles onto the frame halves and then further pulls the retractor frame open to the desired width. The retractor frame cannot be accidentally pulled apart due to the ratchet stops provided. The incision retractor paddles have outwardly curving bottom edge sections which project internally, inside the body wall integument providing additional stability against lifting and torsional forces.

The frame halves have one or more mounting means radiating away from the outside of the frame; onto these mounting means the surgeon can affix mounting jigs with attachment posts. Onto an attachment post the surgeon can affix attachment means for attaching internal organ and tissue retractor paddles. The attachment means has two attachment bores, one bore fits over the attachment post, thereafter an internal organ and tissue retractor paddle handle fits through the second bore which then allows for quick, easy, safe and independent adjustment of the internal organ and tissue retractor paddle in all planes and axes of motion.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein.

Figure 1:
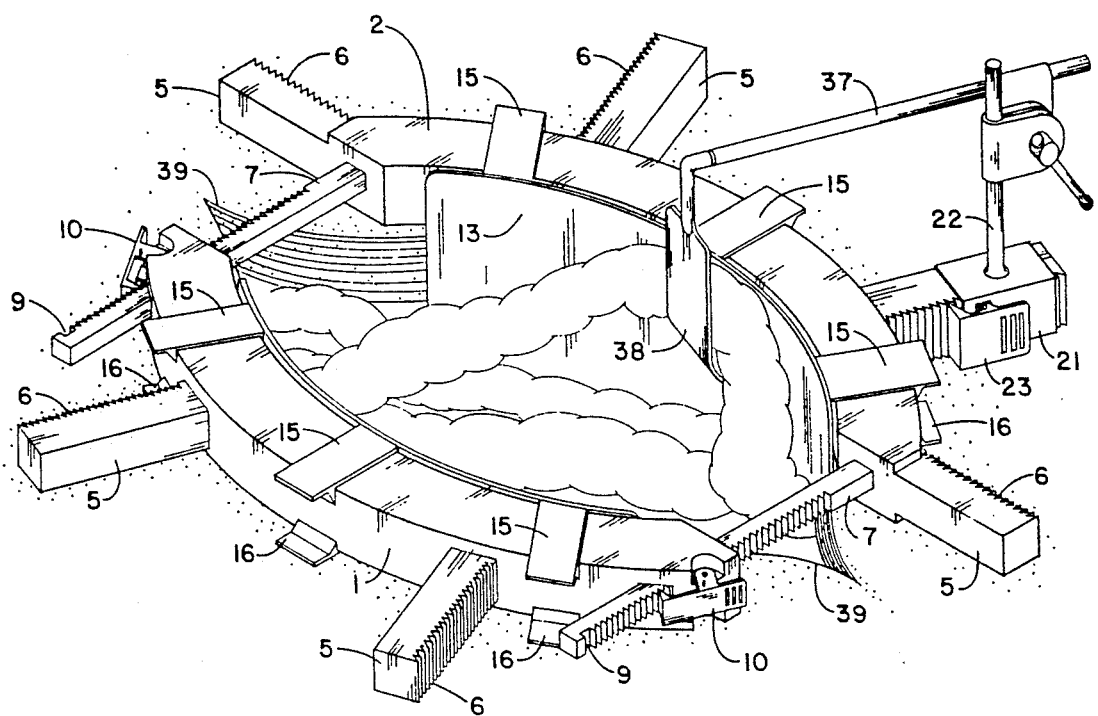
FIG. 1 is a view of the preferred embodiment of the self retaining retractor of the apparatus of the present invention shown in an opened position in a surgical incision.
Figure 2:
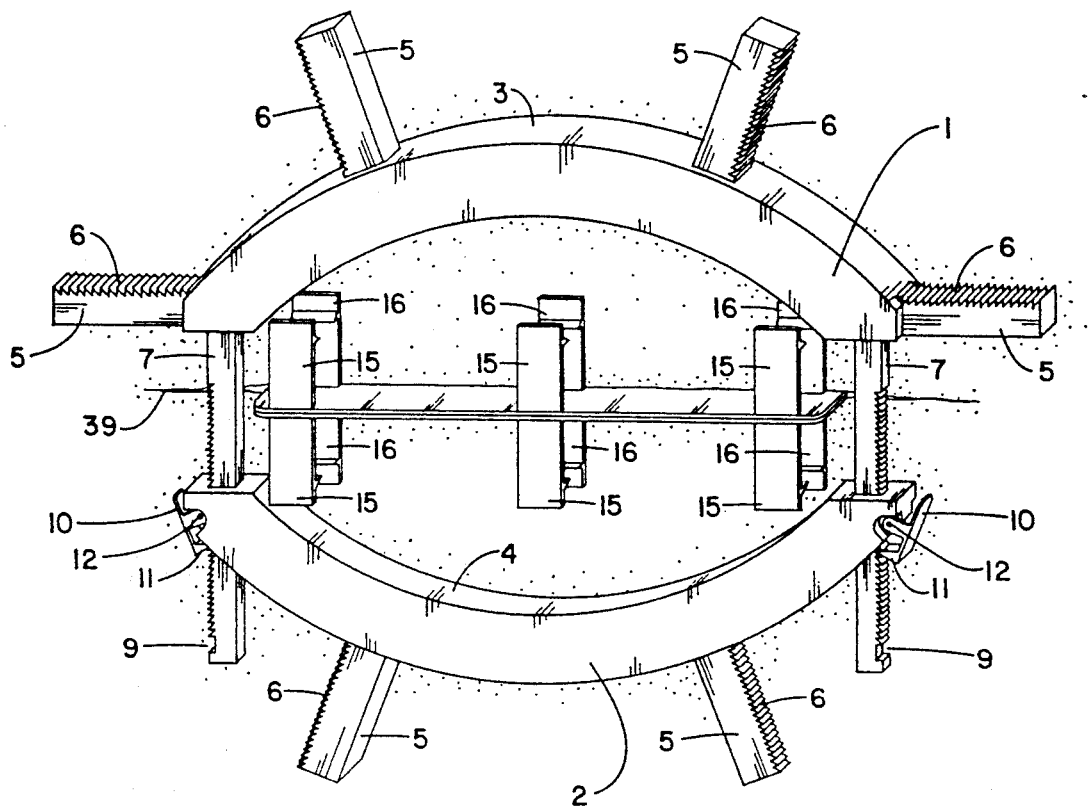
FIG. 2 is a top view of the preferred embodiment of the apparatus of retractor paddles in situ with partially opened retractor frame in place longitudinally over the incision, and prior to attachment to the retractor frame.

DETAILED DESCRIPTION OF THE PREFERRED EMBODIMENT:

FIG. 1 shows an overall view of the self retaining retractor used in a preferred embodiment of incision retraction, retaining and apparatus stabilization along with internal organ and tissue retraction. The assembly includes a rigid frame 1 member with two posts at either end 7, and a similar rigid frame 2 member with bores 20 corresponding to the posts 7 and ratchet clips 10 thereon. The post frame 1 is mated with the bore frame 2 by pushing the posts 7 into the bores 20. The ratchet clips 10 can be tensioned with spring 12 and provided with a catch 11 for engaging ratchet teeth 6. The frame halves 1, 2 are prevented from being accidentally pulled apart due to the ratchet stop 9.

Two appropriately sized resilient, flexible incision retractor paddles 13 are placed into the incision 39. Each paddle 13 can be removably attached to a frame member 1, 2 using spaced apart, horizontal flanges 15, 16. The bottom flange 16 rests on the outside upper surface of the patient's body during use. The depth of the incision retractor paddle 13 is determined, for example, by the thickness of body integument (as from the outside layer of skin to just inside the parietal peritoneum). At this lower depth, the incision retractor paddles curve to provide outwardly extending portions 19, providing additional retaining surface 19 to oppose lifting and torsional forces exerted during assembly and use (particularly internal organ and tissue retraction, see FIG. 1).

Prior to placement, the inside of the incision retractor paddles 13 face each other in situ in the incision 39 flanges 15, 16 are oriented toward the inside of the frame halves 3, 4. During installation, the surgeon manually squeezes the inside face of the pair of the incision retractor paddles 13 respectively onto the retractor frames, 1, 2 making a tight physical connection (and slightly retracting the incision). Flange 15 is placed over the frame section 1 or 2 and flange 16 under the selected frame 1 or 2. The top and bottom flanges 15, 16 each have a catch 17 which engages a frame member 3, 4 as selected and thus attaches the incision retractor paddle 13 onto the selected frame section 1 or 2.

Figure 3:
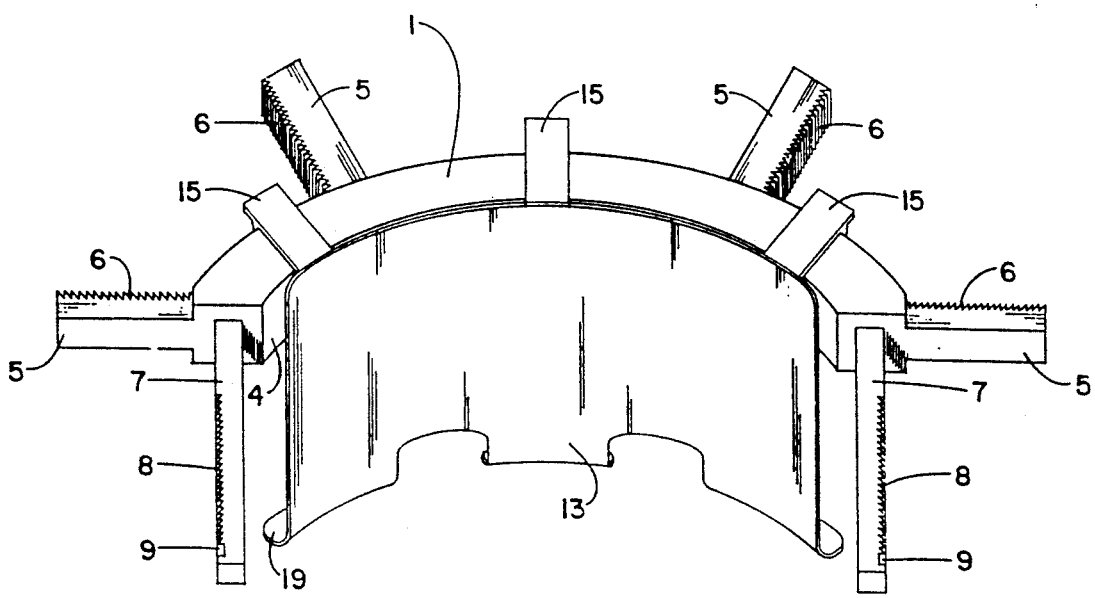
FIG. 3 is a partial perspective view of the preferred embodiment of the apparatus of the present invention illustrating one half of the retractor frame, the retractor posts of the retractor frame, and one incision retractor paddle attached thereto.
Figure 4:
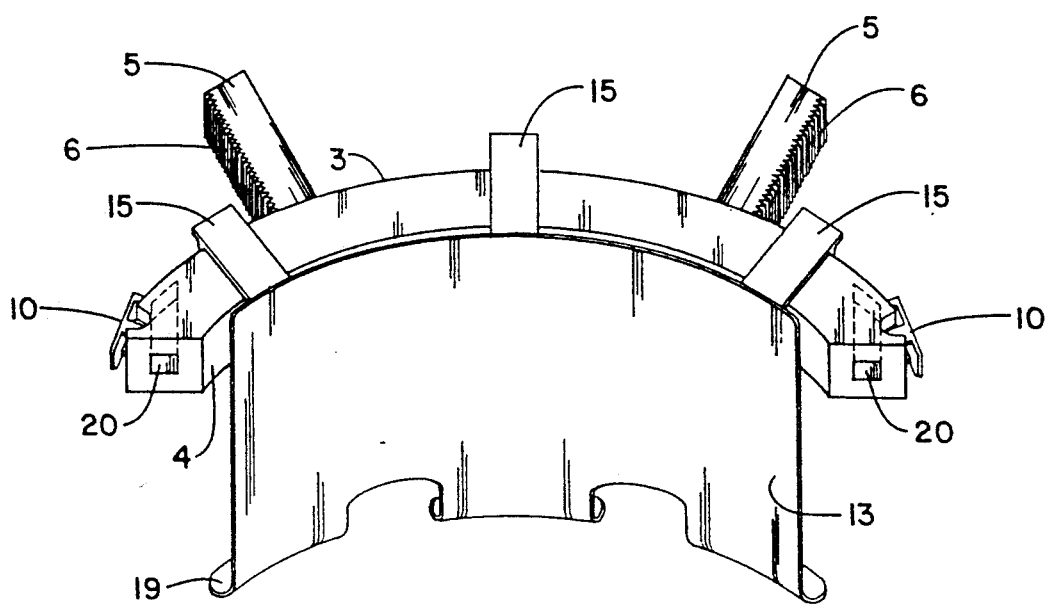
FIG. 4 is a partial perspective view of the preferred embodiment of the apparatus of the present invention illustrating one half of the retractor frame, the retractor bores of the retractor frame, the ratchet clips and one incision retractor paddle attached thereto.

FIGS. 1, 3 and 4 show incision retractor paddles, attached to the frame halves 1, 2.

Figure 5:
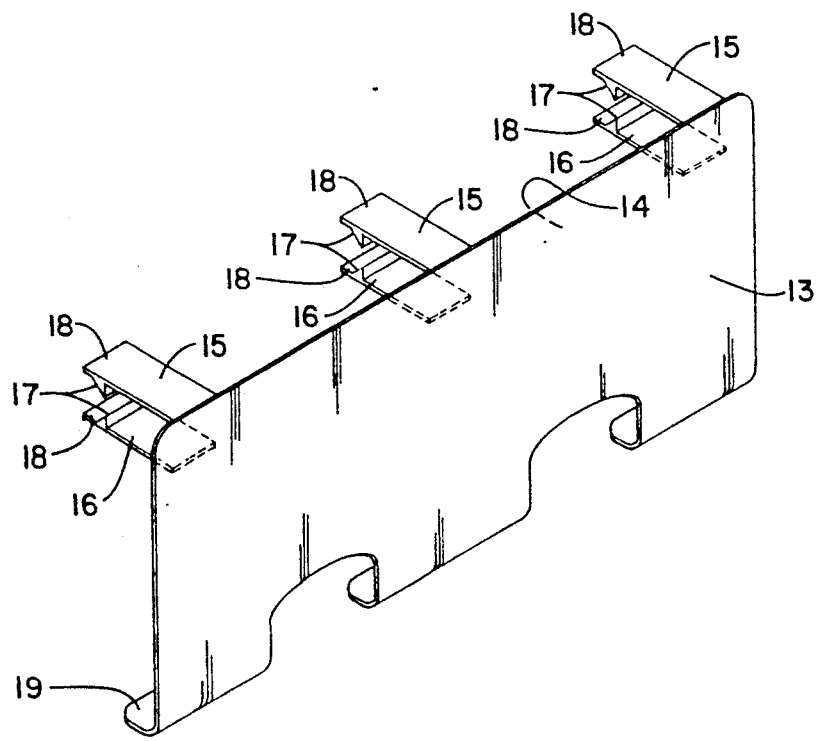
FIG. 5 is a partial perspective view of the preferred embodiment of the apparatus of the present invention illustrating one incision retractor paddle.
Figure 6:
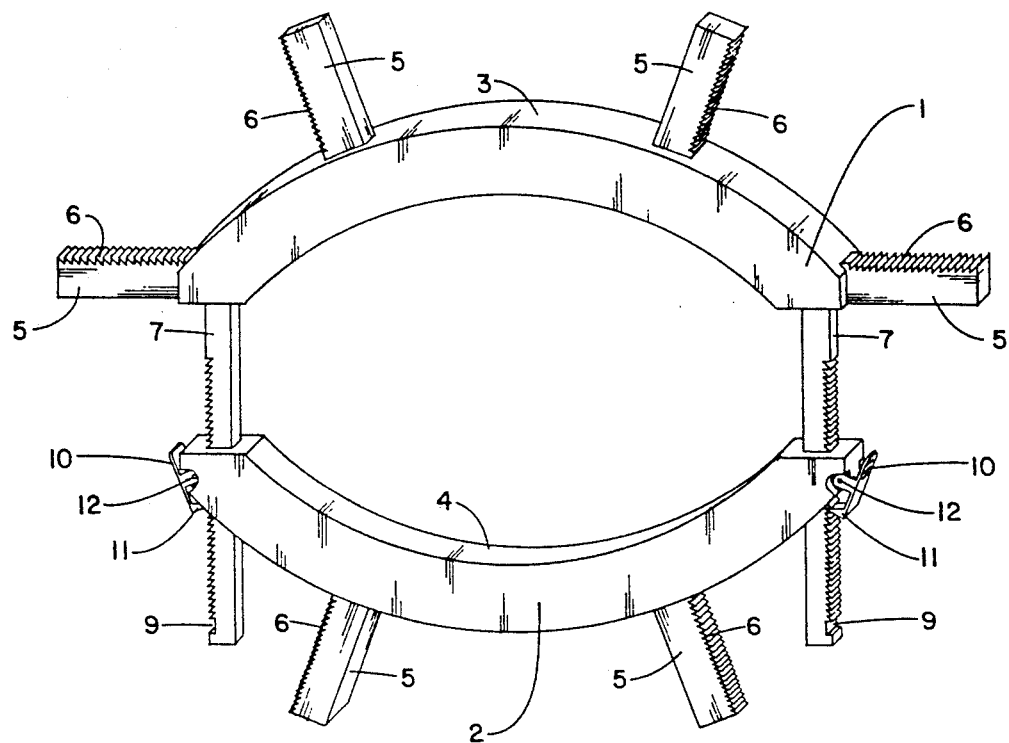
FIG. 6 is a top view of the preferred embodiment of the apparatus of the present invention.

FIG. 5 shows an incision retractor paddle 13, the attachment flanges 15, 16 which hold the incision retractor paddles 13 to the frame halves 1, 2 as well as the outwardly curved portions 19, the catch 17, and flange portions 18 that project beyond the catch 18 for allowing manual disengaging of the attachment flanges 15, 16 from the frame 1 or 2.

The surgeon can to use outward manual pressure on the inside of the incision retractor paddles 13 in situ, spreading the frame halves 1, 2 further apart to the desired incision opening width (see FIG. 1). The clips 10 in contact with the ratchet teeth 8 maintain the desired incision opening width when manual pressure on the inside of the apparatus is released.

The underside of the frames 1, 2 rest against the outside upper surface of a patient's body. The outer surface 14 of each incision retractor paddle is in contact with the wall of the incision 39. The outwardly extending lower end portion 19 is in contact with the internal surface of the body wall integument, and these areas of contact between the paddles 13 and various body tissues stabilize against lifting and torsional forces, which primarily occur during use of internal organ and tissue retractor paddles 38.

With the incision 39 open to the required width, the incision retraction and retention functions have been accomplished, and the apparatus is stabilized and available for internal organ and tissue retraction, FIG. 1.

Figures 7, 8:
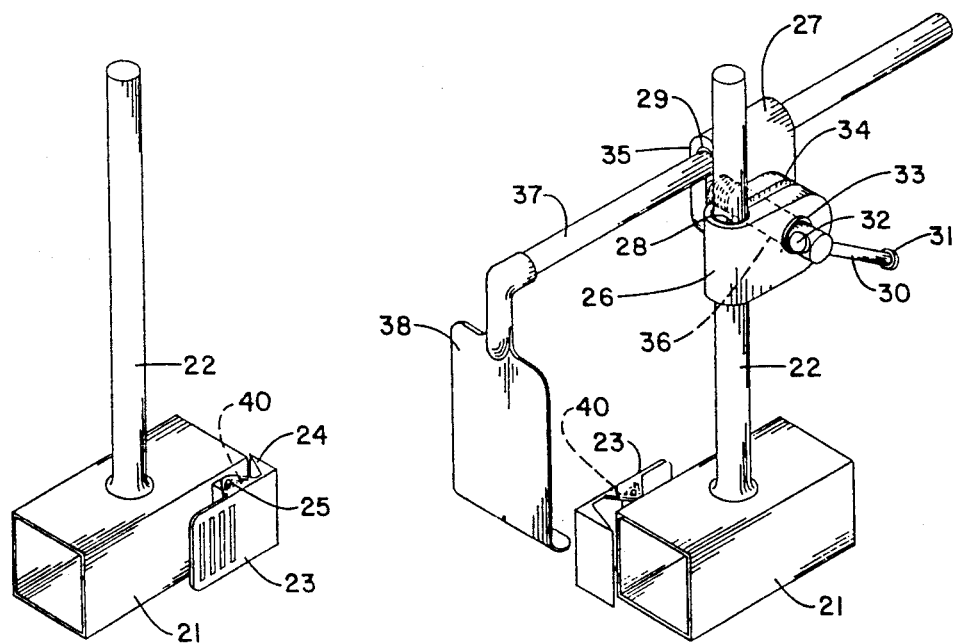
FIG. 7 is a fragmentary perspective view of the mounting jig portion of the preferred embodiment of the apparatus of the present invention showing the attachment post and ratchet clip.
FIG. 8 is a fragmentary perspective view of the preferred embodiment of the apparatus of the present invention illustrating the mounting jig with attachment post, ratchet clip, and with internal organ and tissue retractor handle and paddle in place.

FIG. 7 shows a view of the mounting jig 21 with attachment post 22, and ratchet clip 23 which is mounted at pivot 25 to jig 21, and tensioned using coil spring 40. A catch 24 secures jig 21 to mounting beam 5.

The mounting jig 21 slides onto the mounting beam 5 that extends outwardly from the frame outer surface 3, 4. Ratchet clips 23 are provided with a tensioning spring 40 and catch 24 to prevent inward movement and without raising the ratchet clip 23. The ratchet clip 23 is tensioned to engage against ratchet teeth 6.

FIG. 8 shows an internal organ and tissue retractor paddle 38 attached to a retraction handle 37 which is held in place by mating it through the bore 29 of an attachment bracket 27, which is connected with shaft 36 to a second bracket 26. The second bracket 26 is held in place by mating its bore 28 with the attachment post 22 of the mounting jig 21.

The internal organ retractor paddle 38 is adjusted as desired then fixed in place by tightening the shaft 36 by grasping handle 30 and tightening it into a threaded base of the 27. Shaft 36 has a stop 33 so that tightening can be effected. Handle 30 has end stops 31, 32 allowing the handle 30 to slide inside a transverse bore of the shaft 36, thus altering the length and position of the turning means handle 30. The spaces 34, 35 respectively between opposing legs of each bracket 26, 27 decrease when the shaft 36 is tightened, thus creating a frictional attachment at bores 28, 29 of the brackets 26, 27 and the respective attachment post 22, paddle handle 37 and between the two brackets 26, 27.

Figure 9:
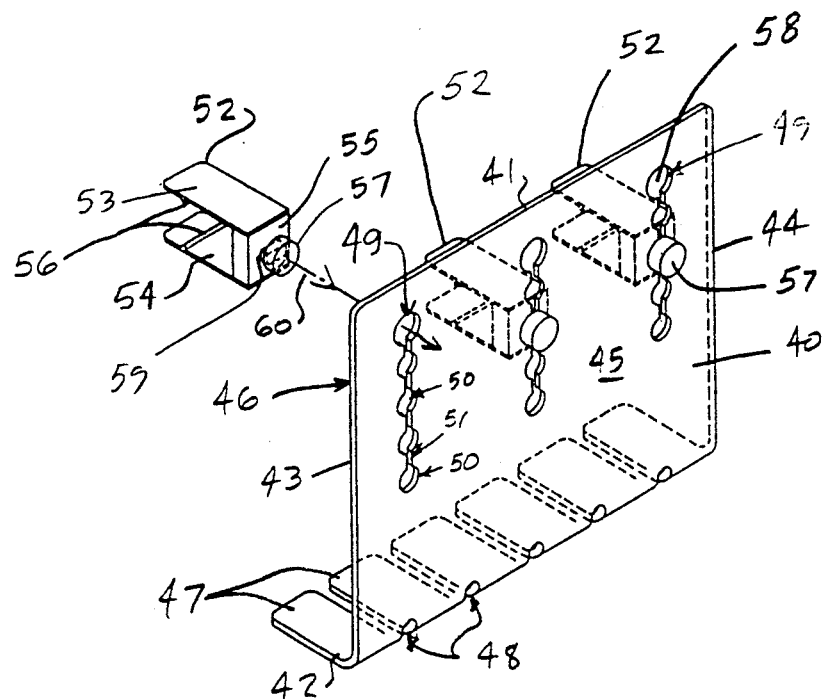
FIG. 9 is a fragmentary view of an alternate embodiment of the apparatus of the present invention illustrating an adjustable incision retractor paddle.
Figure 10:
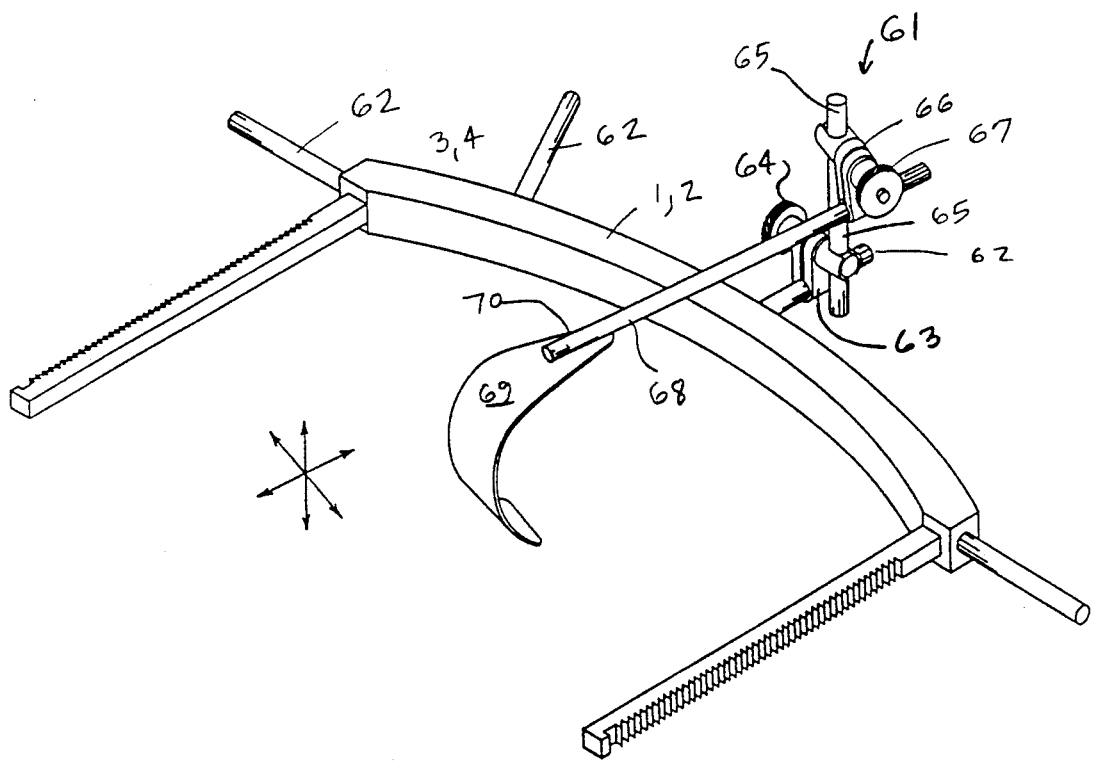
FIG. 10 is a fragmentary perspective view of another alternate embodiment of the apparatus of the present invention illustrating an adjustable jig for supporting a retractor from a position outside of and above the retractor frame.

FIGS. 9-10 illustrate alternate embodiments of the apparatus of the present invention. In FIG. 9, a retractor paddle 40 is generally rectangular in shape, providing an upper 41 and a lower 42 end portion, and spaced apart generally vertically extending side portions 43-44. The paddle 40 provides an inner surface 45 which faces a similar opposing paddle during use. The rear or outer surface 46 engages body tissue during use. The bottom 42 portion provides one or more laterally extending flange members which can have gaps or slots 48 therebetween as shown in FIG. 9.

A plurality of longitudinal or vertically extending slots 49 are placed generally parallel to one another and to sides 43, 44 as shown in FIG. 9. Each slot 49 is comprised of a plurality of circular portions 50 interconnected with rectangular sections 51. Each circular portion 50 of slot 49 represents an adjustment position for clip 52. Clip 52 is comprised of an upper 53 and a lower 54 flange which are generally horizontally extending and are connected with vertical flange 55. Projecting portions 56 on each of the flanges 53, 54 are designed to engage a frame member 1, 2 during use. Because the clip 52 can be fixed in a number of different positions along slot 49, the vertical position of paddle 45 can be varied with respect to a frame section 1, 2 as desired. Further, because each clip 52 can be movable independently of another clip, it is possible that clips 52 can be placed in circular portions 50 of differing elevations such as for example diagonally so that the upper edge 41 of paddle 45 is angularly oriented with respect to a plane defined by the two frames 1, 2 which is typically horizontal.

In summary, the paddle 45 can be adjusted upward or downward and tilted into angular orientations. Each clip 52 provides a circular head portion 57 which is larger in diameter than the circular portions 50 but smaller in diameter than the uppermost circular portion 58 of slot 49. A rectangular member 59 extends between circular head portion 57 and vertical flange 55 on clip 52. The rectangular portion 59 is smaller in size than the rectangular portions 51 of slot 49. Thus, when the clip is rotated ninety degrees (90°) from the orientation shown in FIG. 9, this allows the rectangular portion 59 to pass through any one of the similarly configured rectangular portions 51 of slot 49 and affords vertical adjustability of clip 52 with respect to paddle 45 until head portion 57 aligns with a desired circular portion 50 of slot 49 as desired.

Rectangular member 59 can form an integral connection between vertical flange 55 and circular head member 57 such as for example by adhesive, welding, or integral construction such as by manufacturing vertical flange 55, rectangular portion 59 and circular head portion 57 from a single block of material such as stainless steel or the like.

In FIG. 10, an alternate embodiment of a jig is disclosed, designated generally by the numeral 61. Frame 1, 2 is shown in FIG. 10 as including a plurality of circular post members 62 that extend away from outer surface 3,4 of a particular frame section 1, 2. The posts 62 allow attachment of jig 61 using brackets 63, 64. The bracket 63 attaches to a post 62 and can be tightened using a thumb screw 64 and threaded shaft. Similarly, a vertical post 65 extends between bracket 63 and bracket 66.

A thumb screw 67 can be used to tightened bracket 66 against vertical post 65. Bracket 66 also supports retractor paddle shaft 68 which carries a deep retractor that can be curved as shown in FIG. 10, designated by the numeral 69. The curved retractor paddle 69 attaches to shaft 68 at weld 70 for example.

The embodiment of FIG. 10 allows a retractor to be supported above the plane defined by retractor frame 1, 2 and from a position outside of the area between frames 1, 2 during use i.e. outside of the incision. This is a particular utility in retracting portions of the anatomy such as organs which are disposed within the operative field but which are not supported by retractor paddles 13, 40.

Using the apparatus of FIG. 10, a particular organ can be retracted from a position above and removed from the operative field and in adjustable fashion with regard to multiple angular orientations of the shaft 68. For example, the bracket 63 rotates about the post 62. Similarly, the bracket 66 rotates about the vertical post 65. Also, the shaft 68 rotates in its supporting bracket 66. Thus, by loosening the thumb screws 64, 67, a desired rotational movement of each bracket 64, 66 can be made with respect to shafts 62, 65, and 68. Additionally, the bracket 63 can be moved inwardly and outwardly with respect to frames 1, 2 into a desired adjustable position. Further, the bracket 63, 66 can be moved upwardly and downwardly upon the post 65. Further, the shaft 68 can be moved inwardly and outwardly with respect to the frames 1, 2 and bracket 66.

Figure 11:
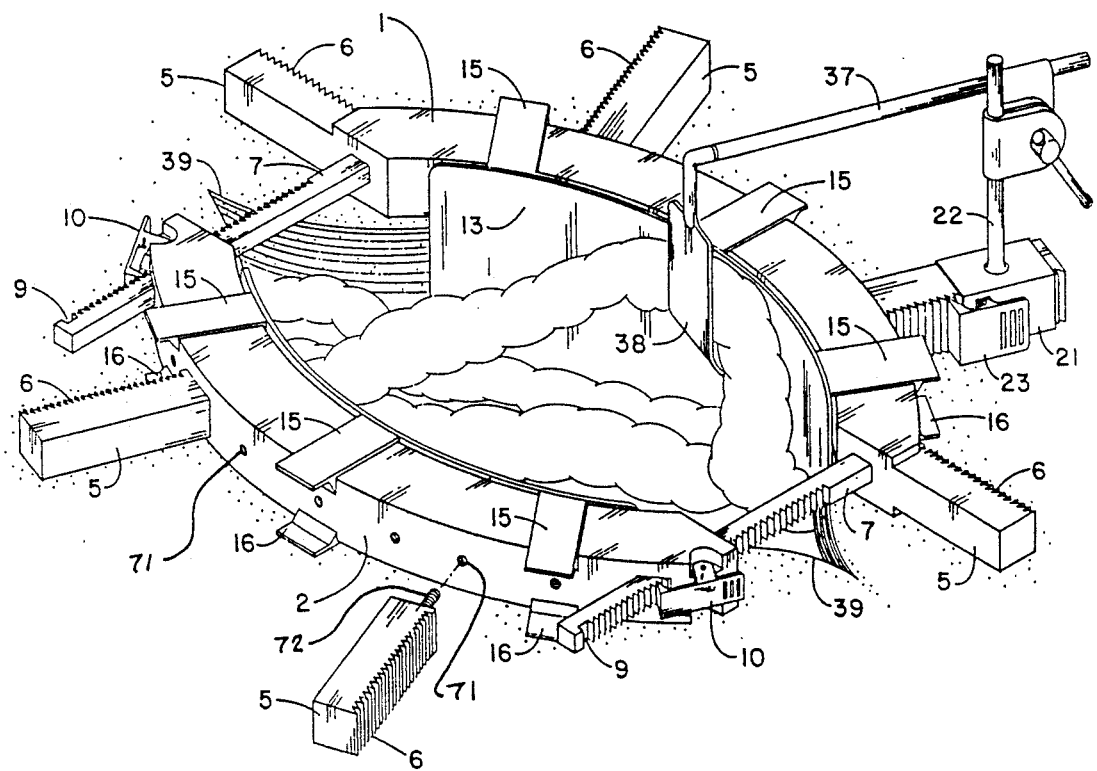
FIG. 11 is a perspective view of another alternate embodiment of the apparatus of the present invention.

In the embodiment of FIG. 11, a plurality of internally threaded openings 71 provide attachment openings for threadably receiving an externally threaded attachment stud that is connected to mounting beam 5 or to post 62. This feature allows selective location of a beam 5 or a post 62 along frame sections 1,2 as shown in FIG. 11. A surgeon can thus selectively locate the beams 5 and posts 62 and the retractors 38,69 to suit a particular patient or a particular operation.

Many other variations, modifications, and alternate embodiments may be made in the apparatus and techniques hereinbefore described, by those having experience in this technology, without departing from the concept of the present invention. Accordingly, it should be clearly understood that the apparatus and methods depicted in the accompanying drawings and referred to in the foregoing description are illustrative only and are not intended as limitations on the scope of this invention, as defined in the following claims.

The following table 1 lists the part numbers and part descriptions as used herein and in the drawings attached hereto.

TABLE 1

| PART NO. | PARTS LIST DESCRIPTION |
| --- | --- |
| 1 | frame |
| 2 | frame |
| 3 | outer surface |
| 4 | outer surface |
| 5 | mounting beam |
| 6 | teeth |
| 7 | post |
| 8 | teeth |
| 9 | stop |
| 10 | clip |
| 11 | catch |
| 12 | spring |
| 13 | paddles |
| 14 | outer surface |
| 15 | attachment flange |
| 16 | attachment flange |
| 17 | catch |
| 18 | projecting portion |
| 19 | lower end |
| 20 | bore |
| 21 | jig |
| 22 | post |
| 23 | clip |
| 24 | catch |
| 25 | pivot |
| 26 | bracket |
| 27 | bracket |
| 28 | bore |
| 29 | bore |
| 30 | handle |
| 31 | end |
| 32 | end |
| 33 | stop |
| 34 | space |
| 35 | space |
| 36 | shaft |
| 37 | handle |
| 38 | paddle |
| 39 | incision |
| 40 | paddle |
| 41 | top |
| 42 | bottom |
| 43 | side |
| 44 | side |
| 45 | inside surface |
| 46 | outer surface |
| 47 | flanges |
| 48 | gap |
| 49 | slot |
| 50 | circular portion |
| 51 | rectangular portion |
| 52 | clip |
| 53 | upper flange |
| 54 | lower flange |
| 55 | vertical flange |
| 56 | projecting portion |
| 57 | head |
| 58 | larger circular opening |
| 59 | rectangular portion |
| 60 | arrow |
| 61 | jig |
| 62 | post |
| 63 | bracket |

TABLE 1-continued

| PART NO. | PARTS LIST DESCRIPTION |
| --- | --- |
| 64 | thumb screw |
| 65 | post |
| 66 | bracket |
| 67 | thumb screw |
| 68 | shaft |
| 69 | retractor paddle |
| 70 | weld |
| 71 | internally threaded opening |
| 72 | externally threaded stud |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A surgical retractor comprising:
   a) a rigid retractor frame for use with a patient's tissue after an incision has been formed to define a surgical opening, the frame comprising two opposed frame halves defining a plane, and that are movable with respect to each other, each of the frame halves having an inside surface that abuts the incision during use, an outer surface that faces away from the incision during use, and an upper surface, and wherein the inside surfaces and upper surfaces of each frame half define an operative zone that allows a surgeon free access to the incision;
   b) retraction means, removably attached to the inside surface of the retractor frame and prior to final retraction of body tissue; and
   c) auxiliary retractor mounting means, attached to the outer surface and radiating away from the retractor frame and surgical opening during use, the auxiliary retractor mounting means including a post member generally vertically positioned and extending above the plane and at a position spaced outwardly of the frame outer surface.

2. The surgical retractor as recited in claim 1 wherein the auxiliary retractor mounting means includes one or more mounting jigs removably attachable to the vertically positioned posts, and said auxiliary retractor mounting means further includes internal organ and tissue retraction means affixed to the jigs during use so that one end of the internal organ and retraction means attaches to a mounting jig at a position above the plane, and spaced away from the incision and outwardly of the outer surface.

3. A surgical retractor as recited in claim 1 wherein:
   a) the rigid frame halves are provided at each end with posts and borings which are of matching dimension and cross section so that the posts can affix to the borings;
   b) said posts and borings being aligned on each frame half so as to mate the post of one frame half into the boring of the opposite frame half;
   c) said posts being provided with successive ratchet grooves faced so that a frame half affixed with a tensioned ratchet clip would be allowed outward movement away from the opposing frame half and retarded from inward movement toward the opposing frame half; and d) the end(s) of the frame half bearing boring(s) is (are) provided with a tensioned ratchet clip and catch which engages the ratchet grooves on the aforesaid posts.

4. A surgical retractor comprising:
a) a rigid retractor frame for use with a patient's tissue after an incision has been formed to define a surgical opening, comprising two opposed frame halves defining a plane, and that are movable with respect to each other;
b) retraction means, removably attachable to the retractor frame and prior to final retraction of body tissue;
c) mounting means radiating away from the retractor frame and surgical opening;
d) the rigid frame halves are provided at each end with posts and borings which are of matching dimension and cross section;
e) said posts and borings being aligned on each frame half so as to mate the post of one frame half into the boring of the opposite frame half;
f) the posts being provided with successive ratchet grooves; and
g) a ratchet stop at the terminal end of the post which prevents accidental separation of the frame halves.

5. A surgical retractor as recited in claim 4 wherein
a) a rigid retractor frame for use with a patient's tissue after an incision has been formed to define a surgical opening, comprising two opposed frame halves defining a plane, and that are movable with respect to each other;
b) retraction means, removably attachable to the retractor frame and prior to final retraction of body tissue;
c) mounting means radiating away from the retractor frame and surgical opening;
d) the rigid frame halves are provided at each end with posts and borings which are of matching dimension and cross section;
e) said posts and borings being aligned on each frame half so as to mate the post of one frame half into the boring of the opposite frame half;
f) said posts being provided with successive ratchet grooves faced so that a frame half affixed with a tensioned ratchet clip would be allowed outward movement away from the opposing frame half and retarded from inward movement toward the opposing frame half; and
g) end of the frame half bearing borings are provided with a tensioned ratchet clip and catch which engages the ratchet grooves on the aforesaid posts.

6. A surgical incision retraction paddle for use with a retractor frame, comprising:
a) a flexible and resilient paddle body formed into a planar surface having a top and an outside surface that faces away from the incision during use;
b) said paddle body being equipped at top on the outside with flexible and resilient attachment means;
c) said attachment means comprising flexible extensions of the outside paddle body substantially perpendicular to the planar surface of the paddle;
d) said flexible extensions comprising pairs of upper and lower flexible extensions parallel to each other and equipped with retaining catch means and projections beyond the catch;
e) said catch means being designed to clip onto the retractor frame and to be retained thereon by tension or friction; and
f) said projections extending beyond the catch means for allowing manual disengagement of the catch means from the frame; and
g) wherein the paddle body is provided with one or more outwardly curved bottom edge sections for the retention of tissue and stabilization of the paddle and frame within an incision.

7. A surgical retractor comprising:
a) a rigid retractor frame for retracting a patient's tissue after an incision has been formed to define a surgical opening, comprising two opposed frame halves defining a plane, and that are movable with respect to each other;
b) incision retraction means, removably attachable to the retractor frame and prior to final retraction of body tissue; and
c) retractor mounting means, radiating away from the retractor frame and surgical opening for supporting additional retractors at a position spaced away from the incision and frame holders, and above the plane; and
d) one or more additional retractors, each having a proximal end portion for deep retraction of tissue and a distal portion supported above the plane at a position spaced outwardly of the frame.

8. The surgical retractor as recited in claim 7 further comprising:
a) mounting jigs removably attachable to the retractor mounting means, and each jig including one or more attachment posts that can be vertically extended and that are affixed to said mounting jigs laterally away from the frame; and
b) the additional retractors including internal organ and tissue retraction means, affixed by separate mounting jigs to the attachment posts.

9. A surgical retractor as recited in claim 8 wherein:
a) the rigid frame halves are provided at each end with posts and borings which are of matching dimension and cross section so that the posts can affix to the borings;
b) said posts and borings being aligned on each frame half so as to mate the post of one frame half into the boring of the opposite frame half;
c) said posts being provided with successive ratchet grooves faced so that a frame half affixed with a tensioned ratchet clip would be allowed outward movement away from the opposing frame half and retarded from inward movement toward the opposing frame half; and
d) the end(s) of the frame half bearing boring(s) is (are) provided with a tensioned ratchet clip and catch which engages the ratchet grooves on the aforesaid posts.

10. A surgical retractor as recited in claim 7 wherein the posts are provided with successive ratchet grooves with a ratchet stop at the terminal end of the post which acts to prevent accidental separation of the frame halves.

11. A surgical incision retraction device comprising:
a) a frame comprised of frame halves connectable together and expandable apart into multiple fixed adjustment positions;
b) multiple flexible and resilient paddle bodies, each having a planar retractor surface;

c) each said paddle body being equipped with attachment means for removably affixing each paddle body to a respective frame half;
d) said attachment means comprising flange extensions extending outside the paddle body during use in a direction away from the incision, and substantially perpendicular to the planar surface of the paddle;

e) said flange extensions comprising pairs of upper and lower extensions parallel to each other and equipped with retaining flange means for gripping the frame;
f) the flanges defining catch means for gripping the top and bottom of the frame; and
g) said catch means being manually disengagable from the frame.

* * * * *